United States Patent [19]

Larock

[11] 4,113,755

[45] Sep. 12, 1978

[54] SYNTHESIS OF PROSTAGLANDIN PRECURSORS

[75] Inventor: Richard C. Larock, Ames, Iowa

[73] Assignee: Iowa State University Research Foundation, Ames, Iowa

[21] Appl. No.: 798,092

[22] Filed: May 18, 1977

[51] Int. Cl.$^2$ .............................................. C07F 15/00
[52] U.S. Cl. .............................. 260/429 L; 260/429 R
[58] Field of Search ......................... 260/429 R, 429 L

[56] References Cited

U.S. PATENT DOCUMENTS

| 3,369,035 | 2/1968 | Schultz | 260/429 R |
|---|---|---|---|
| 3,398,168 | 8/1968 | Medema | 260/429 R |
| 3,446,825 | 5/1969 | Schultz | 260/429 R |
| 3,705,919 | 12/1972 | Heck | 260/429 R |
| 3,783,140 | 1/1974 | Heck | 260/431 X |
| 4,065,479 | 12/1977 | Larock | 260/429 L |

OTHER PUBLICATIONS

Horino et al., Tetrahedron Letters, No. 8, pp. 647–650, (1974).

Primary Examiner—Helen M. S. Sneed
Attorney, Agent, or Firm—Zarley, McKee, Thomte, Voorhees & Sease

[57] ABSTRACT

A process of making prostaglandin precursors by reacting bicyclic or polycyclic olefins with an alkenylmercuric salt, in the presence of a noble metal salt to provide a cis, beta-alkenyl bicyclic alkyl noble metal salt.

8 Claims, No Drawings

SYNTHESIS OF PROSTAGLANDIN PRECURSORS

BACKGROUND OF THE INVENTION

The prostaglandins are an extremely important, biologically active class of C-20 unsaturated hydroxy acids discovered first in the 1930's by Goldblatt and Von Euler in extracts of human seminal fluid and sheep vesicular glands. Due to the difficulties in isolating and determining the structures of milligram quantities of these compounds, it was not until the 1960's that their structures were determined. By then, the extreme physiological activity of these compounds was evident, and the desire for larger amounts of these valuable compounds for biological testing and stimulated organic chemists to tackle the formidable problem of synthesizing these highly functionalized molecules. Within a few short years a number of total syntheses of all of the primary prostaglandins had appeared led by the work of Professor E. J. Corey and his group at Harvard (see U. Axen, J. E. Pike and W. P. Schneider in "The Total Synthesis of Natural Products", Vol. 1 J. ApSimon, Ed., Wiley-Interscience, New York, 1973, pp. 81–142, which is incorporated herein by reference).

With the ready availabiliy of these compounds for the first time, extensive biological testing ensued. Prostaglandins have subsequently been found to have pronounced effects on the cardiovascular and renal systems; the respiratory tract; the eye, skin, lungs and bone; and the reproductive organs. Within the cardiovascular system alone, they apparently play a central role in regulating blood platelet aggregation, blood pressure and flow, cardiac output, heart rate, and vascular activity. While prostaglandins appear to have pharmacological potential in the treatment of asthma, nasal congestion, stomach ulcers, inflammation, hypertension, thrombosis, etc., considerable attention so far has focused on their possible use in the induction of labor, termination of pregnancy, and possible utility in contraception.

To date the major drawbacks to clinical application of the prostaglandins have been the very broad range of physiological activity prevalent in these compounds and their brief duration of action due to rapid metabolic deactivation. The desire for longer lasting drugs exhibiting much more specific activity has recently produced a number of very interesting analogs of prostaglandins and many structure-activity studies have resulted. The interesting synthetic work of J. Fried at Chicago on oxa analogs, and recent synthesis of 8-, 12-, and 15-methyl prostaglandins which are blocked from undergoing the usual metabolic deactivation should be noted in this regard. Fried et al., *Ann. N.Y. Acad. Sci.*, 180, 38 (1971) which is incorporated herein by reference. Some of these synthetic analogs will hopefully find clinical application.

Tremendous potential also exists in the development of prostaglandin antagonists and reagents which will inhibit prostaglandin bio-synthesis and metabolism. At present only a few prostaglandin antagonists are known. The best known and most studied are the dibenzoxazepine derivatives, especially SC-19220; phosphorylated polymers of phloretin, especially polyphloretin phosphate; and oxa- and thia- prostaglandin analogs, particularly 7-oxa-13-prostynoic acid. Considerable recent interest has also developed in potential antagonists of prostaglandin biosynthesis. In fact, it has been suggested that the biological activity of antiinflammatory, analgesic and antipyretic drugs can be explained by the fact that they inhibit the biosynthesis of prostaglandins. It is therefore possible that the synthesis of specific inhibitors of prostaglandin biosynthesis and prostaglandin receptor antagonists could produce some clinically useful drugs.

For these reasons there has been considerable work of late on the biosynthetic pathways involved in the formation of prostaglandins.

Although the natural prostaglandins show promise as potential drugs, there are a number of problems. For instance, they are metabolized very rapidly within the body. Studies on humans show that prostaglandin $E_2$, a smooth muscle contractor, that is used to induce labor or terminate pregnancy, when given intraveneously at 96° activated in the first 90 seconds after administration. A more perplexing problem is the lack of tissue specificity of the prostaglandins. Prostaglandin $E_2$, in addition to causing uterine smooth muscle to contract to induce labor, causes gastrointestinal smooth muscle to contract leading to cramps and diarrhea. This same compound, when aspirated into the nostrils, immediately dilates the bronchi and alleviates asthmatic attack, but at the same time it irritates the mucous lining of the throat, causing pain and coughing.

The therapeutic potential of the prostaglandins and the lack of an abundant natural source of these compounds has led to a number of laboratory investigations to provide a total synthesis as a method of obtaining them. In addition, because of their lack of specificity in inducing pharmacological activity, it has been thought desirable to develop significant analogs of prostaglandin compounds which would be more stable than natural prostaglandins, and which would have more specificity in providing pharmacological activity. Accordingly, it is an object of this invention to provide prostaglandin like compounds which may be convenient synthetic precursors which are thermally stable and can be prepared at good yield levels.

Yet another object of this invention is to provide prostaglandin precursors which can selectively be reacted to provide either exo or endo analogs of prostaglandins.

Yet another object of this invention is to provide a convenient and simple synthesis route for preparing precursors of prostaglandin compounds by reacting norbornene or related bicyclic olefins with a vinylmercuric salt in the presence of a palladium salt to provide A-B-vinylnorbornyl palladium salt which is thermally stable and contains both the vinyl and palladium groups exo (as opposed to natural prostaglandins normally having one exo bond and one endo bond), and therefore subject to different stereochemistry than natural prostaglandins.

SUMMARY OF THE INVENTION

A new synthetic route to prostaglandin precursors employing vinylmercurials as intermediates. Preferably vinylmercuric halides are reacted with norbornene in the presence of a palladium (II) salt to give an isolable, thermally stable, sigma-norbornyl palladium chloride compound.

DETAILED DESCRIPTION OF THE INVENTION

The overall synthesis method of this invention may be represented by the following equation:

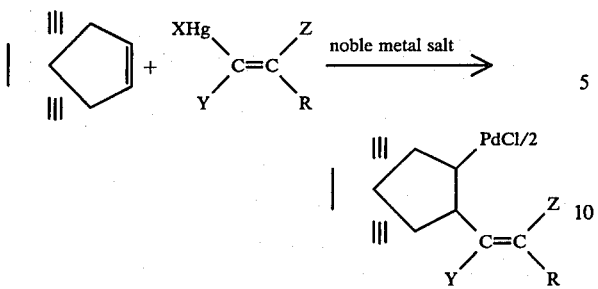

In word description, the reaction is a reaction between a norbornene type compound, such as norbornene itself as depicted in the above equation, and an alkenylmercuric salt, such as the vinylmercuric chloride depicted in the above equation, to provide a sigma bonded B-alkenyl norbornyl noble metal salt. The resulting product is an exo product, that is the bonds indicated by the dark lines are both coming out of the plane from the remaining portion of the molecule. In most natural prostaglandins, the upper bond is below the plane of the main portion of the molecule while the lower one is above it, i.e., the relationship is endo, exo, respectively. This slightly different stereochemistry has the potential for leading to some interesting therapeutic properties for the prostaglandin analogs of this invention. Of course, however, during subsequent synthesis reactions, to provide the preselected prostaglandin analog, the exo-endo relationships can be varied if desired.

The first starting material for the prostaglandin precursor synthesis of this invention is norbornene itself, a substituted norbornene compound or a related bicyclic olefin.

Norbornene is a seven carbon bicyclic compound containing one unsaturated bond having the technical chemical name of bicyclo[2.2.1]hep-2-ene. The dotted line bonds shown in the pictoral representation of norbornene in the previously presented equation represents bonds extending below the plane of the five member ring and can stereochemically speaking be represented in the following manner:

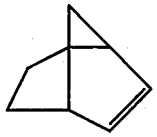

While norbornene is the most commonly employed starting material, it should be understood that other bicyclic olefins may also be utilized, for example, norbornadiene and other related bicyclic olefins such as bicyclo[3.2.1]oct-6-ene and bicyclo-[2.2.2]oct-2-ene. Bicyclo octenes as just described are similar in reactivity to norbornene and differ structurally only in that they have a second carbon atom in the bicyclic bridge. Also it should be understood that substituted norbornene compounds may also be utilized successfully as a starting reactant without interfering with the basic reaction method of this invention. Of course, however, the carbon atoms of the unsaturated olefin bond of the norbornene must remain unsaturated in order that the addition reaction with the vinylmercuric compound, as depicted above, will occur. However, substitutions on all of the carbon moieties of the norbornene may occur.

Thus, there may be oxo substitutions, nitrogen substitution, alkyl group substitution, keto substitution, alcoholic substitution or the like, the possibilities being almost limitless. The critical factor being that only the reaction site remain unsaturated.

The second reaction starting material is an alkenylmercuric salt which may be represented by the following formula:

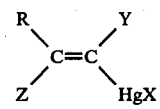

Preferably the alkenylmercuric salt is a vinylmercuric halide in which R, Y and Z may be selected from the group consisting of hydrogen, alkyl, aryl, and aralkyl and halides. Preferably they are lower $C_1$ to $C_8$ moieties. In the most preferred reaction which employs vinylmercuric halides, Y and Z are both hydrogen. This reaction is preferred because of its similarity to the actual side chains present in the natural prostaglandins and the ease of preparation of these vinylmercuric halides.

X represents the anion of the vinylmercuric salt. While it has been most often referred to as a halide salt, it is to be understood that other salts could be utilized, the halide salt being mentioned herein for repesentative purposes only. However, it is preferred that X be a halide moiety such as chloride, bromide, or iodide, and most preferably is chloride. Other monovalent anions which could be used are acid sulfate, dihydrogen phosphate, acetate, and other non-oxidizing anions which would not interfere with the basic reaction synthesis of the invention.

The vinylmercuric halide starting material is readily available through acetylene addition reactions. See for example:

R. C. Larock and H. C. Brown, *J. Organometal Chem.*, 36, 1 (1972).

R. C. Larock, S. K. Gupta, and H. C. Brown, *J. Amer. Chem. Soc.*, 94, 4371 (1972).

H. Staub, K. P. Zeller, and H. Leditschke, in Houben-Weyl's "Methoden der Organischen Chemie" 4th Ed., Vol. 13, G. Thieme Verlag, Stuttgart, 1974, Pt. 2b, pp. 192–199.

The above are incorporated herein by reference.

As depicted in the overall reaction equation shown above, the reaction is conducted in the presence of a noble metal salt. Since the noble metal salt is employed as a reaction addition reagent, the amount employed is at least a reaction equivalent amount. Noble metal salts of palladium, rhodium, platinum and iridium may be employed. In other words, the group 8 noble metal salts may be employed as addition salts for this reaction. It is, however, preferred that the salt be a palladium (II) salt since they seem to react best, are the least expensive, and most readily commercially available.

Where the preferred palladium (II) salts are employed, forming the prostaglandin precursors of this invention, the palladium (II) salts may have any of the conventional anions. They include the halides, such as chloride, bromide, and iodide, the sulfates, the nitrates, the acetates, the phosphates propionates and others known to those skilled in the art. In summary, the precise anion of the palladium salt employed is not critical.

It is preferred that the reaction be conducted in the presence of an alkali metal salt, as well as the palladium salt. The employment of an alkali metal salt in addition to the palladium salts helps in dissolving the palladium salt. Best results are obtained when the alkali metal salt is a metal halide such as the chloride or bromide as illustrated by sodium chloride, potassium bromide, lithium chloride, lithium bromide, and the like. Most preferably the palladium (II) salt is a palladium halide salt and a reaction equivalent amount of the salt is employed with the addition of a lithium halide salt as well. The most preferred salt is palladium chloride and it is preferred that the reaction be conducted in the presence of lithium chloride. In this instance the reaction ingredient is often referred to as lithium palladium chloride, having the formula:

$$Li_2PdCl_4$$

The added metal salt when one is employed, may be added to the reaction mixture separately or alternatively added jointly with the palladium salt in the form of a coordination complex such as the lithium palladium chloride.

As heretofore briefly mentioned, it is preferred that the vinylmercuric salt be a halide salt, and it is also preferred that the palladium (II) salt be a halide salt, with both salts having the same halide anion. This is so simply in order to prevent the prostaglandin precursors synthesized by the process of this invention from having a mixture of anion moieties in the resulting compound.

The reaction preferably is conducted in the presence of an organic solvent in order to provide more intimate contact between the reactants. The solvent must be a polar reaction solvent which is inert to the reaction ingredients. Suitable solvents which may be employed are tetrahydrofuran, methyl alcohol, diethyl ether, hexamethylphosphoramide, acetonitrile and the like. It is also preferred that the reaction be conducted in the presence of an excess of the norbornene reaction ingredient. By "excess" it is meant that the amount of the norbornene reaction ingredient employed be in excess of the stoichiometric amount. Since one reaction equivalent is a stoichiometric amount for the reaction of the present invention, it is preferred that more than one reaction equivalent of the norbornene compound be employed, and up to as many as ten reaction equivalents. Employment of greater than stoichiometric amounts of the norbornene reaction ingredient seems to assure the production of the desired prostaglandin precursor at good yield levels.

The reaction is conducted in the presence of a solvent since the reactants are often solid. It is a rapid reaction and it may be conducted under relatively mild reaction conditions. The reaction may be conducted at temperatures of from approximately −40° C up to room temperature or even higher with satisfactory results. The reaction may be conducted most typically at atmospheric pressure but if desired, other pressure conditions may be employed, although little advantage is gained. In addition, the reaction may be conducted under inert gases to provide a wholly inert environment for the reaction. Time is also not a critical factor for the reaction of this invention, and the reaction may be conducted within a variety of time limits. In most cases, the reaction is completed within an hour or so and typically much faster, although if desired, overnight reaction times may be employed.

The prostaglandin precursor products are solid derivatives and may be recrystallized to provide the pure compounds in high yields. The precursors may be used to make A, B, C, D, E, or F series prostaglandins. For a discussion of the naming of the prostaglandins and a brief background discussion of the various uses for some of these compounds, see *Chemical and Engineering News,* June 24, 1974, at pages 18 through 20, which are incorporated herein by reference.

As previously mentioned, the above outlined synthesis procedure for preparation of bicyclic prostaglandin analogs, provides compounds which are useful for the synthesis of natural occurring prostaglandins such as the F series and many analogs thereof. As an example of this synthesis route, a synthesis for $PGF_{2\alpha}$ will be outlined.

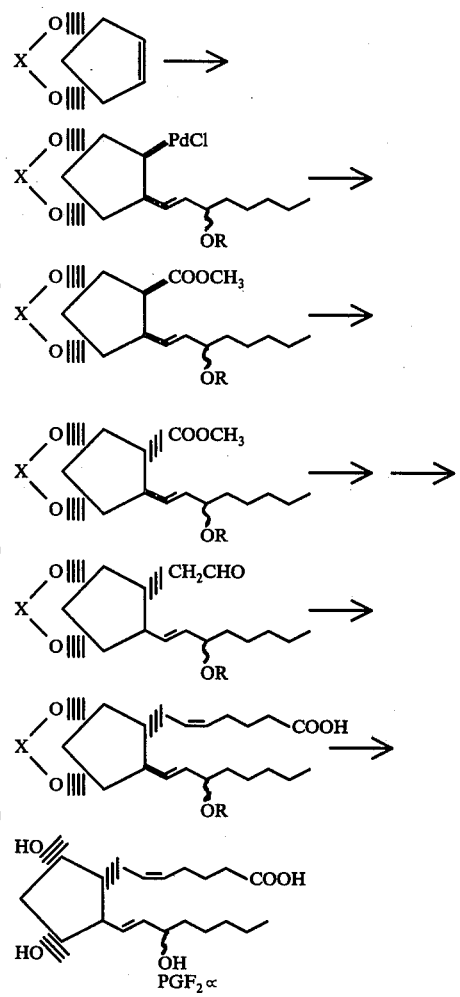

It has been found that the prostaglandin precursors are unusually thermally stable, can be obtained in high yields, are not prone to give adverse side reactions, and surprisingly, can be synthesized with both side chains in an exo position.

Having now described the reaction in terms of its general conditions as well as specific descriptive details for each of the reaction ingredients, the following specific examples are offered to further illustrate but not limit the process of this invention.

EXAMPLES 1 to 5

1.77 grams (10 mmol) Palladium chloride, 0.85 grams (20 mmol) lithium chloride, and 9.5 grams (100 mmol) norbornene were weighed into a well-dried 250 ml. round bottom flask equipped with a septum inlet, nitrogen inlet tube, and a magnetic stirring bar. After flushing with nitrogen, 100 ml. dry tetrahydrofuran was added by syringe.

After cooking in an ice water bath, 3.19 grams trans-3,3-dimethyl-1-butenylmercuric chloride (10 mmol) was added all at once, while backflushing with nitrogen. The well stirred reaction mixture was allowed to slowly warm to room temperature and then stirred overnight. Ether and activated carbon were added to the reaction mixture which was filtered and washed with saturated ammonium chloride. The combined washings were re-extracted with ether and the combined ether extracts dried over anhydrous sodium sulfate. Upon removal of the solvent, a crude pale yellow solid was obtained, 2.85 grams (89%).

Five different examples employing norbornene (Examples I though (V) and a substituted norbornene compound Example V) as the starting material and employing the vinylmercuric halides as depicted in the following table were run. The compounds which were synthesized, that is the resulting prostaglandin precursor, for the sake of convenience, are designated herein as I through V. I, II and III were recrystallized from chloroform. IV was recrystallized from methylene chloride, V was washed with pentane until a pale yellow solid remained. V was isolated as a crude oil. To the extent that conditions varied from those described above, they are shown in the table. The crude yield is given for the compounds, with the recrystallized yield, where it was obtained, in parentheses. The numbers under each reaction ingredient refer to the number of mmol. Where ml is indicated, that refers to, of course, milliliters of the solvent. THF refers to tetrahydrofuran.

TABLE

| | Norbornene type Compound | Vinyl mercuric Salt | Solvent Noble Metal Salt | % Yield (Recrystallized yield) Prostaglandin Precursor | |
|---|---|---|---|---|---|
| I. | 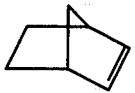 | +  | 1 $\xrightarrow{\text{Li}_2\text{PdCl}_4}{\text{THF}}$ | 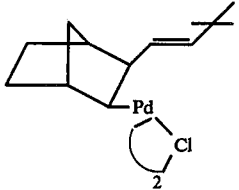 | |
| | | 10 : 1<br>10 : 1<br>10 : 1 | 100 ml.<br>100 ml.<br>100 ml. | I | 89 (39)<br>89 (49)<br>50 |
| II. |  | + 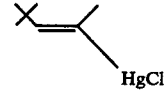 | 1 $\xrightarrow{\text{Li}_2\text{PdCl}_4}{\text{THF}}$ | 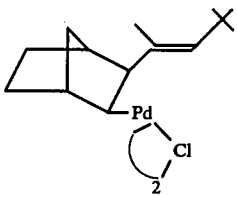 | |
| | | 10 : 1 | 100 ml. | II | 88 (58) |
| III. |  | + 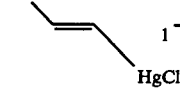 | 1 $\xrightarrow{\text{Li}_2\text{PdCl}_4}{\text{THF}}$ | 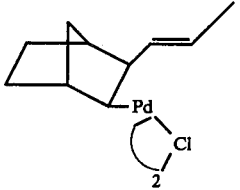 | |
| | | 10 : 1 | 100 ml. | III | 88 (49) |
| IV |  | +  | 1 $\xrightarrow{\text{Li}_2\text{PdCl}_4}{\text{THF}}$ | 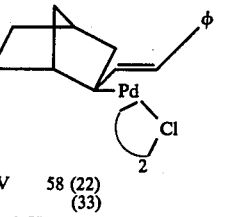 | |
| | | 10 : 1<br>10 : 1 | 100 ml. | IV | 58 (22)<br>(33) |
| V. | 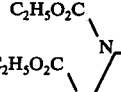 | 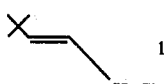 | 1 $\xrightarrow{\text{Li}_2\text{PdCl}_4}{\text{THF}}$ | 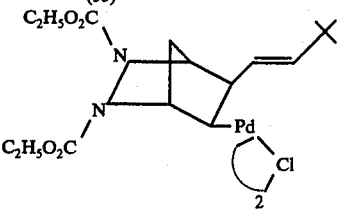 | |

TABLE-continued

| Norbornene type Compound | Vinyl mercuric Salt | Solvent | Noble Metal Salt | % Yield (Recrystallized yield) Prostaglandin Precursor |
|---|---|---|---|---|
| | 1:1 | 100 ml. | | V 45 (15) |

It should be understood that certain modifications may be made in the description and examples above presented without departing from the scope and spirit of the present invention. For example, it should be possible to employ direct hydroboration mercuration in a one pot synthesis to prepare the vinylmercuric halide without a separate and distinct isolation of this compound. As a result, a step in the sequence, namely the preparation of the vinylmercuric halide salt starting material could be eliminated. Other modifications could conceivably also be made; however, the overall reaction synthesis of a norbornene type compound with an alkenylmercuric salt is employed in every instance.

What is claimed is:

1. A process of making prostaglandin precursors, which comprises:
   reacting a norbornene type compound selected from the group consisting of norbornene, substituted norbornene compounds and norbornene related bicyclic olefins, with an alkenyl mercuric halide, in the presence of a noble metal salt to provide a cis-(beta)-alkenyl bicyclic noble metal salt.

2. The process of claim 1 wherein said norbornene type compound is norbornene.

3. The process of claim 1 wherein said noble metal salt is a palladium salt.

4. The process of claim 3 wherein the amount of said palladium salt is at least a reaction equivalent amount.

5. The process of claim 4 wherein reaction is conducted in the presence of a soluble alkali metal salt.

6. The process of claim 1 wherein said mercuric halide is a compound of the formula:

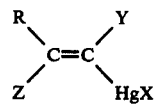

wherein R, Y and Z are organic radicals selected from the group consisting of hydrogen, alkyl, aryl, and aralkyl and halides.

7. The process of claim 5 wherein X is a halide.

8. A process of making thermally stable, exo, precursors of prostaglandins, which comprises:
   reacting norbornene, or a substituted norbornene compound with a vinylmercuric halide salt, in the presence of a palladium salt, to provide a cis-B-vinyl-exo-norbornyl palladium salt.

* * * * *